(12) United States Patent  
Gillam et al.

(10) Patent No.: US 8,589,187 B2
(45) Date of Patent: Nov. 19, 2013

(54) AUTOMATED CLUSTERING FOR PATIENT DISPOSITION

(75) Inventors: Michael T. Gillam, Washington, DC (US); Renato R. Cazangi, Rockville, MD (US); Alexey P. Kontsevoy, Rockville, MD (US); Uri Kartoun, Washington, DC (US); Hao Fang Wu, Chevy Chase, MD (US)

(73) Assignee: Microsoft Corporation, Redmond, WA (US)

( * ) Notice: Subject to any disclaimer, the term of this patent is extended or adjusted under 35 U.S.C. 154(b) by 156 days.

(21) Appl. No.: 12/979,363

(22) Filed: Dec. 28, 2010

(65) Prior Publication Data

US 2012/0166208 A1    Jun. 28, 2012

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ........................................................ 705/2–3
See application file for complete search history.

(56) References Cited

U.S. PATENT DOCUMENTS

| | | | |
|---|---|---|---|
| 5,924,074 A * | 7/1999 | Evans | 705/3 |
| 6,347,329 B1 * | 2/2002 | Evans | 709/202 |
| 6,724,933 B1 * | 4/2004 | Lin et al. | 382/164 |
| 7,123,137 B2 | 10/2006 | Heck et al. | |
| 8,135,740 B2 * | 3/2012 | Friedlander et al. | 707/780 |
| 2004/0236604 A1 * | 11/2004 | McNair | 705/2 |
| 2007/0106534 A1 | 5/2007 | Molinaro et al. | |
| 2008/0284582 A1 | 11/2008 | Wang et al. | |
| 2009/0216556 A1 | 8/2009 | Martin et al. | |
| 2009/0299766 A1 * | 12/2009 | Friedlander et al. | 705/3 |
| 2011/0077968 A1 * | 3/2011 | Kelly et al. | 705/3 |

OTHER PUBLICATIONS

Boger, Zvi., "Finding patient cluster attributes using auto-associative ANN modeling", Retrieved at << http://ieeexplore.ieee.org/xpl/freeabs_all.jsp?arnumber=1223984 >>, Proceedings of the International Joint Conference on Neural Networks, Jul. 20-24, 2003, pp. 2643-2648.

Chipara, et al., "Reliable Patient Monitoring: A Clinical Study in a Step-down Hospital Unit", Retrieved at << http://cse.wustl.edu/Research/Lists/Technical%20Reports/Attachments/901/mobisys09.pdf >>, Technical Report, WUCSE-2009-82, Dec. 2009, pp. 14.

* cited by examiner

*Primary Examiner* — Michael Fuelling

(57) ABSTRACT

The described concepts relate to automated patient disposition. One example can receive a clinician's disposition for a patient. This implementation can perform parameter-based cluster analysis on the patient and a set of patients to identify a sub-set of the patients with which the patient has a high similarity. This example can also cause a graphical user interface to be generated that conveys parameters from the sub-set of the patients and the patient.

7 Claims, 10 Drawing Sheets

GUI 400

Name: John Smith          Patient Id: ABC123
402
404
Cluster analysis details: Parameters  ☑
406          408          410
Parameter name    Considered    Change
412 → DOB              No           Include ← 502
414 → Age              No           Include ← 504
416 → Sex              Yes
418 → Dx code          Yes
420 → Dx description   Yes
                                    506      508
422 → WAIT TIME        Yes          Exclude   Re-analyze
• • •

FIG. 5

GUI 600

Name: John Smith          Patient Id: ABC123

602
Results unchanged

604
Cluster analysis indicates the patient is more similar to patients admitted to the ICU ward than to patients admitted to the Non-ICU ward

FIG. 6

AUTOMATED CLUSTERING FOR PATIENT DISPOSITION

BACKGROUND

The present discussion relates to patient care. For instance, one profoundly fragile but consequential decision in hospitals is related to making decisions around the disposition of a patient. For example, such decisions can relate to when to discharge from the emergency department, versus admit, when to discharge from the hospital, when to transition from one part of the hospital to another, etc. Patient disposition is a complex and subtle decision with profound implications to the patient. One such scenario relates to "Failure to Rescue". Failure to rescue refers to the phenomena where a patient is not transferred to the intensive care unit (ICU) soon enough and instead suffers cardiac or respiratory arrest on a non-ICU floor. Failure to Rescue is estimated to occur across the U.S. at a rate of almost 300,000 cases per year.

In an attempt to remedy this phenomenon, today many emergency medicine rooms (EMRs) manually implement a series of rules to check whether a discharge might be dangerous. These rules may check for critical lab values or abnormal vital signs. The challenge is that there could be hundreds or thousands of rules that need to be written to cover the thousands of known lab tests available today. Yet when all those rules are written, there is also a factorial of interactions between those labs that may also be predictive of danger. Further, new laboratory tests and new knowledge on how to use those tests is entering healthcare at an exponential rate.

SUMMARY

The described implementations relate to automated clustering for patient disposition. One example can receive a clinician's disposition for a patient. This implementation can perform parameter-based cluster analysis on the patient and a set of patients to identify a sub-set of the patients with which the patient has a high similarity. This example can also cause a graphical user interface (GUI) to be generated that conveys parameters from the sub-set of the patients and the patient.

Another example can identify a patient that is subject to a disposition decision. This example can also perform cluster analysis on the patient and a set of patients to make a determination whether the patient is more likely to match a first sub-set of the patients that received a first disposition or is more likely to match a second sub-set of patients that received a second disposition.

The above listed examples are intended to provide a quick reference to aid the reader and are not intended to define the scope of the concepts described herein.

BRIEF DESCRIPTION OF THE DRAWINGS

The accompanying drawings illustrate implementations of the concepts conveyed in the present application. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the Figure and associated discussion where the reference number is first introduced.

FIGS. 1-12 show examples of scenario in which the automated patient disposition concepts can be employed in accordance with some implementations.

DETAILED DESCRIPTION

Overview

Figure 1:
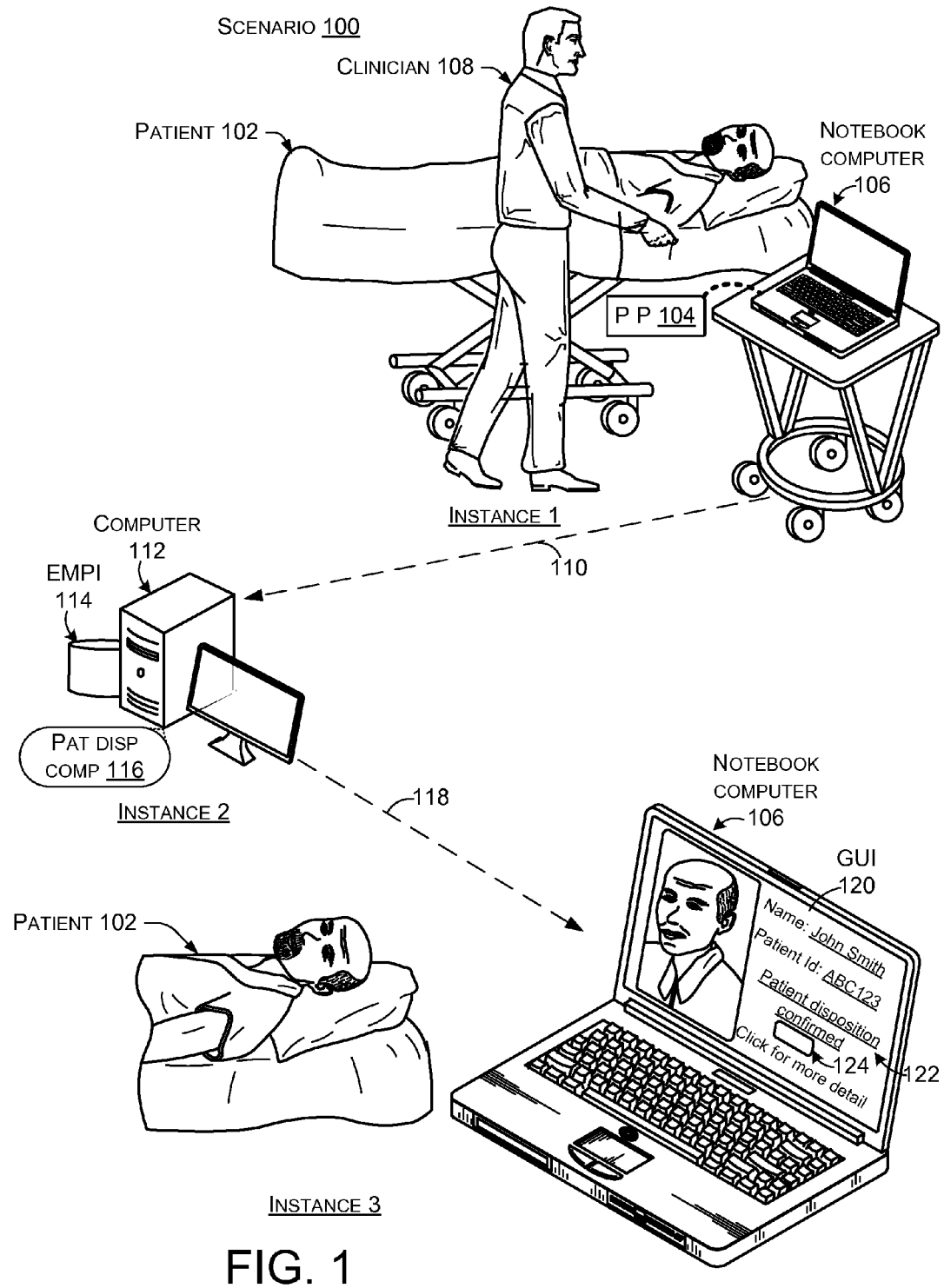

This patent relates to automated clustering for patient disposition. In this document, "disposition" is used to mean any decision regarding patient care. In the health care setting a patient is characterized via a multitude of parameters, such as age, sex, vital sign values such as body temperature, pulse rate, blood pressure, respiratory rate, and lab observations such as chloride, hemoglobin, glucose, etc. The parameters can be recorded in the patient's file. Patient files can be stored in an electronic master patient index (EMPI) or other database. Thus, a large amount of data is available for making healthcare decisions relating to an individual patient or a population of patients. Traditionally, a clinician draws on past experiences and knowledge to weigh the parameters and make decisions regarding patient care. While clinicians tend to be highly caring and highly skilled, such decisions are not readily verifiable. Not being able to verify the decisions can let mistakes go undetected.

The present implementations can utilize automated clustering techniques to either verify the clinician's recommendation or to suggest an alternative disposition. The automated clustering techniques described herein can achieve this functionality by comparing the patient medical situation to other patients based upon some or all of the recorded parameters. For instance, the automated clustering techniques may identify that the patient is more similar to one group or cluster of patients than to another cluster of patients. The level of similarity denoted also as the similarity score, may be determined based on multiple weighted parameters. The automated clustering techniques can then recommend that the patient's disposition should match that of the patients in the first group rather than those in the second group. Thus, the clinician's recommendation is verified if the recommendation matches the recommendation for patients of the first cluster. In contrast, the clinician can be advised to reconsider the recommendation if his/her disposition matches those of patients of the second cluster.

Further, the automated clustering techniques can be presented in a transparent manner to the clinician. In some cases, the presentation can be transparent in that the clinician can view which parameters were included and/or which parameters were excluded in the automated clustering techniques. The clinician may be more inclined to trust the automated clustering techniques when the clinician is able to examine how the results were obtained. Thus, the clinician may be more confident in the results of the automated clustering techniques. As such, in a case where the automated clustering techniques recommend a different disposition for the patient than the clinician, the clinician may be more inclined to change his/her initial patient disposition based upon the transparency of the automated clustering techniques. In summary, the present automated clustering techniques can enhance the patient care decision making process and thereby enhance patient health. The above initial discussion is expanded and clarified below by way of several example scenarios described relative to FIGS. 1-12.

Scenario Examples

The discussion above broadly introduces automated patient disposition processing in health care scenarios. To aid the reader in understanding these concepts, scenario 100 provides a tangible example to which the concepts can be applied.

Scenario 100 involves instances 1-3, each of which is discussed below. Starting at instance 1, example scenario 100 involves a patient 102 that presents for care, such as in an emergency room of a health care facility. Assume that the patient is triaged and that various patient parameters 104, such as age, sex, heart rate, blood pressure, etc., are entered into notebook computer 106.

At this point a decision can be made regarding the next step in the patient's care. Stated another way, the patient is a candidate for disposition. For instance, the patient could be sent home, admitted to a non-ICU ward, admitted to an ICU ward, and/or prescribed a medication, among other options. Assume that a clinician 108 decides to admit the patient to a non-intensive care (non-ICU) ward. As indicated by arrow 110, the patient parameters 104 and the clinician's disposition can be sent to computer 112.

In instance 2, computer 112 can receive the clinician's disposition for the patient and the patient parameters. Computer 112 can be communicatively coupled to an EMPI 114. The computer can be programmed to store the patient's parameters 104 in the patient's file in the EMPI. Further, computer 112 can include a patient disposition component 116. The patient disposition component can utilize some or all of the patient parameters to compare the patient to other patients in the EMPI 114. The patient disposition component can perform cluster analysis to determine whether the patient is more similar to a first sub-set of the patients that received the same disposition or is more similar to a second sub-set of patients that received a different disposition. In this case, assume that the patient 102 is more similar to the first sub-set of patients that received the same disposition. Thus, the patient disposition component 116 has confirmed the clinician's patient disposition utilizing cluster analysis. Patient disposition component 116 can cause the determination to be presented to the clinician back on notebook computer 106 as indicated by arrow 118.

In instance 3, a graphical user interface (GUI) 120 that shows the patient's name and patient ID is presented. The GUI 120 also shows at 122 that the clinician's patient disposition is confirmed. More details about the performed cluster analysis can be obtained by selecting icon 124.

Figure 2:
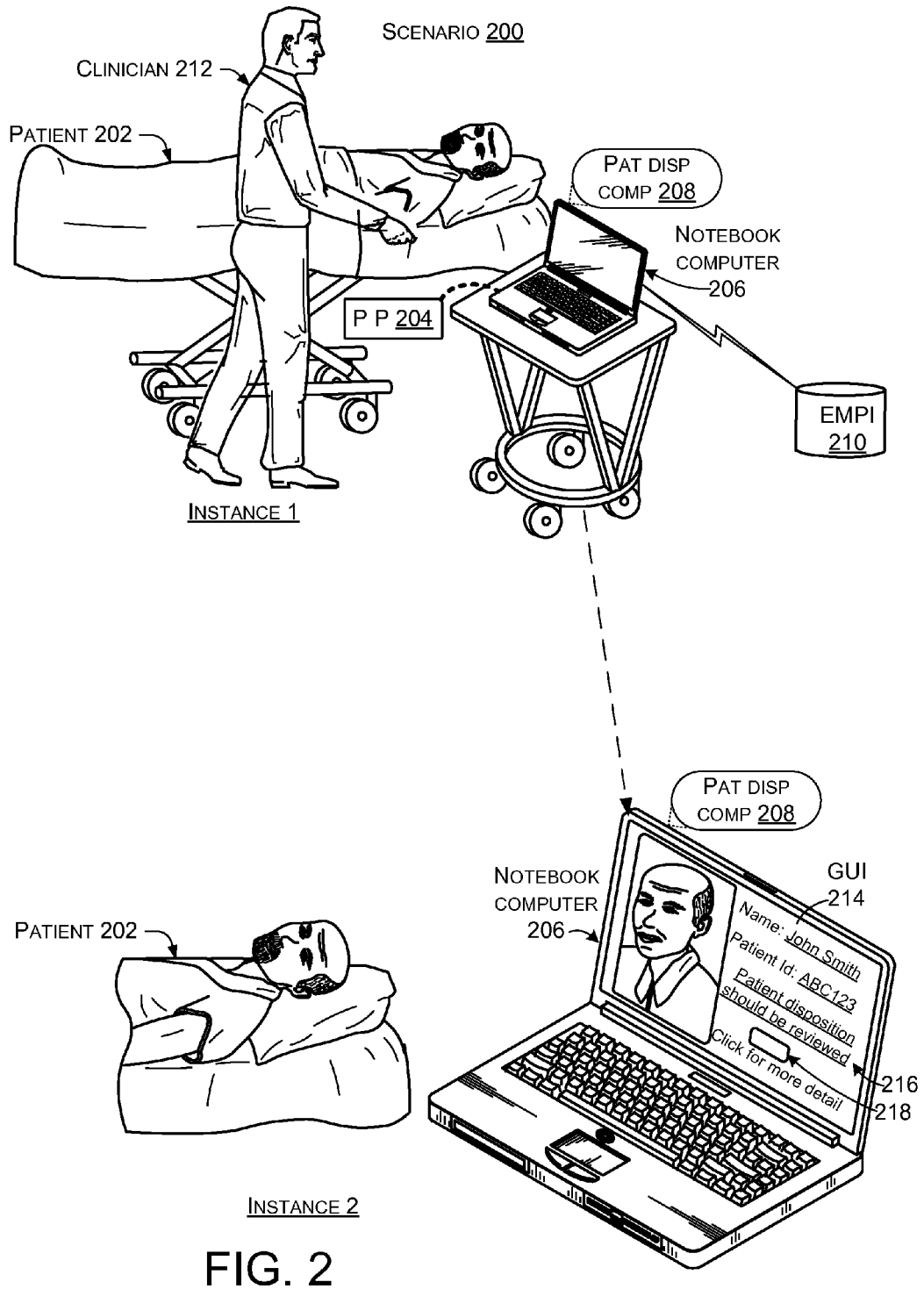
Figure 3:
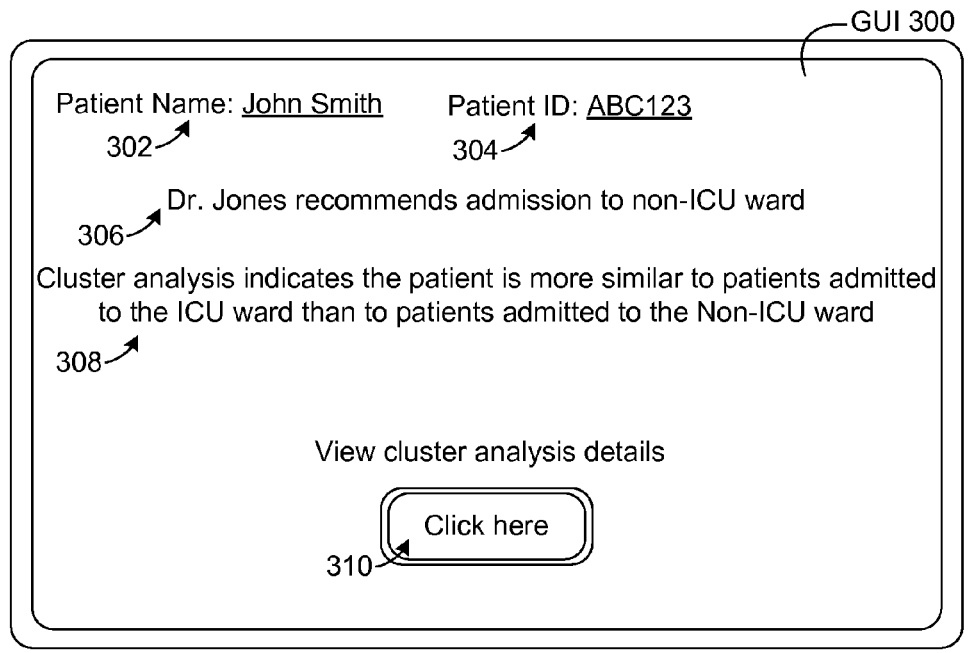
Figure 4:
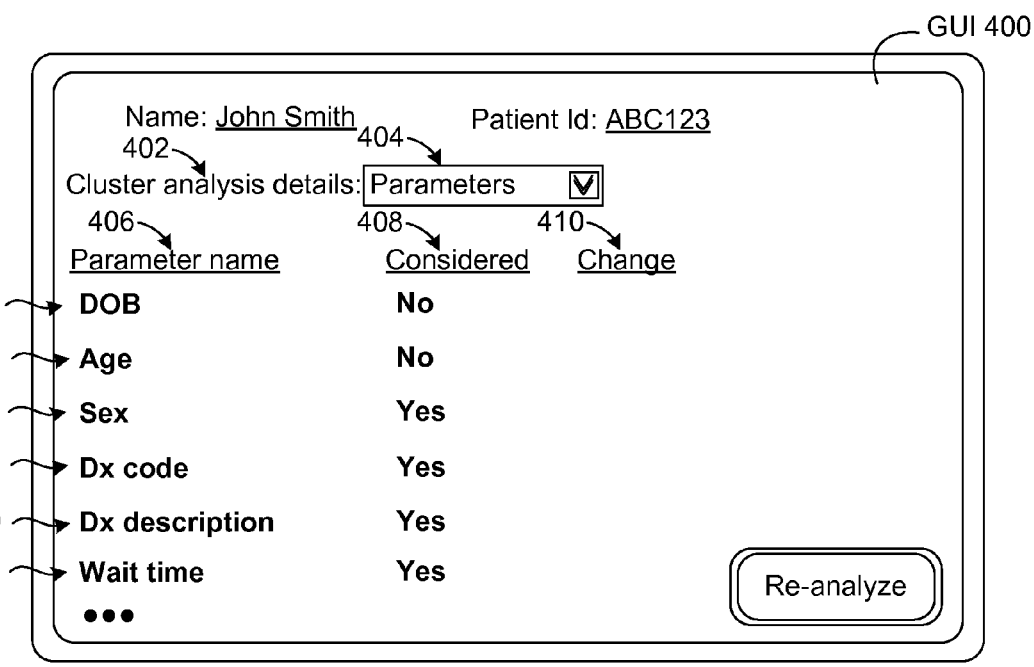

FIGS. 2-4 collectively illustrate another scenario 200 in which automated patient disposition processing can be employed. FIG. 2 is described relative to instances in a similar fashion to FIG. 1, above. FIGS. 3-6 are GUIs produced responsive to instance 2 of FIG. 2.

FIG. 2 shows scenario 200 that involves instances 1-2, each of which is discussed below. Starting at instance 1, example scenario 200 involves a patient 202 that presents for care at a health care facility or in the field. While in this example, patient 200 can be thought of as a new patient, such need not be the case. For instance, in another example, the patient could present for care following an operation or upon daily rounds.

In this example, assume that patient 202 is triaged and that various patient parameters 204 are entered into the patient's file in notebook computer 206. In this case, notebook computer 206 includes a patient disposition component 208. The patient disposition component 208 can communicate with an EMPI 210 to access other patient files. For instance, the patient disposition component may communicate with the EMPI via a network, such as a cellular network, a closed system such as a local area network or the Internet, among others.

At this point a decision can be made regarding the next step in the patient's care. For instance, the patient could be prescribed a specific medication at a specific dose, admitted, sent home, etc. Continuing with the above example, assume that clinician 212 decides to admit the patient to a general (e.g., non-ICU) ward of the facility.

In this case, the patient disposition component 208 has access to the parameters 204 and the clinician's decision to admit to a non-ICU ward. The patient disposition component can obtain parameters from patient files in the EMPI 210 and automatically perform cluster analysis relative to the patient. Note that the patient disposition component 208 may also consider parameters from the patient's file in the EMPI in addition to the parameters 204 that were recently obtained from the patient. For instance, the patient's file may indicate that the patient is an organ transplant recipient even though no information regarding such a parameter was obtained during the present triage of the patient.

The patient disposition component 208 can determine a cluster of patients with which patient 202 is similar (and potentially most similar). The patient disposition component can determine what dispositions were applied to patients in this cluster. The patient disposition component can then compare the patient dispositions from the EMPI to the clinician's recommendation. Assume in this case, that the clinician's disposition recommendation for patient 202 does not match the patient dispositions from the cluster. The patient disposition component can cause these findings to be presented for the clinician.

Instance 2 shows such a case, where a GUI 214 is presented on notebook computer 206. The GUI indicates at 216 that the clinician should review his/her disposition for the patient. The GUI 214 also offers the clinician the opportunity to see more details surrounding these findings by selecting box 218. Assume for purposes of explanation that the clinician wants to see more details about the findings on GUI 214 and clicks on box 218.

FIG. 3 shows a GUI 300 generated responsive to the clinician's desire for more information relative to FIG. 2. In this example, GUI 300 shows the patient's name at 302 and the patient ID at 304. At 306, the GUI restates the clinician's recommendation as "Dr. Jones recommends admission to non-ICU ward". At 308, the GUI indicates that "Cluster analysis indicates the patient is more similar to patients admitted to the ICU ward than to patients admitted to non-ICU ward". Thus, the statements at 306 and 308 summarize why the clinician may want to (or should) reconsider the disposition decision. The clinician can obtain further details by clicking box 310. Assume further that the clinician wants more details and clicks box 310.

FIG. 4 shows another GUI 400 generated responsive to the clinician's selection of box 310 as described above. In this case, GUI 400 offers categories of cluster analysis details at 402. Here, the cluster analysis details are set to "Parameters" in a drop down window 404, but other details could be viewed. Parameter information is grouped into a parameter name column 406, a considered column 408, and a change column 410. A partial listing of parameters is listed under the parameter name column 406. This listing includes data of birth (DOB) row 412, an age row 414, sex row 416, a diagnostic (Dx) code row 418, a Dx description 420, and a wait time row 422, among others. Moving across the DOB row 412 to the considered column 408 shows a "no" entry (e.g., DOB was not included as one of the parameters that was considered in the cluster analysis). Similarly, the age parameter was not considered, but the sex, Dx code, Dx description, and wait time parameters were considered. Assume here that the clinician decides that the wrong parameters were considered in the cluster analysis and the clinician wants to adjust the parameters to enhance the clinical relevancy of the cluster analysis results.

FIG. 5 shows a subsequent view of GUI 400 where the clinician has specified to change the status of several of the parameters. In this example, as indicated at 502, the clinician has specified that the DOB parameter should be included. Similarly at 504 the clinician has indicated that the age parameter should be included. Also, at 506 the clinician has indicated that the wait time parameter should not be included. The clinician can then re-run the cluster analysis by clicking the re-analyze button 508. The results are shown in FIG. 6.

FIG. 6 shows a subsequent GUI 600 that shows the updated results of the cluster analysis using the parameters specified by the clinician. In this case, GUI 600 indicates generally at 602 that the results are unchanged. At 604 the GUI specifies that "cluster analysis indicates that the patient is more similar to patients admitted to the ICU ward than patients admitted to the non-ICU ward". In summary, the present implementation can offer transparency of process to the clinician so that the clinician is more likely to trust the results generated by the implementation. In this case, transparency of process is achieved by making a listing of the parameters that were considered and not considered in the cluster analysis. Further, this implementation can allow the clinician to adjust the parameters that are utilized in the cluster analysis. This latter feature can further enhance the clinician's confidence in the cluster analysis results.

FIGS. 7-10 collectively offer an alternative implementation to the implementations described above relative to FIGS. 4-6.

Figure 7:
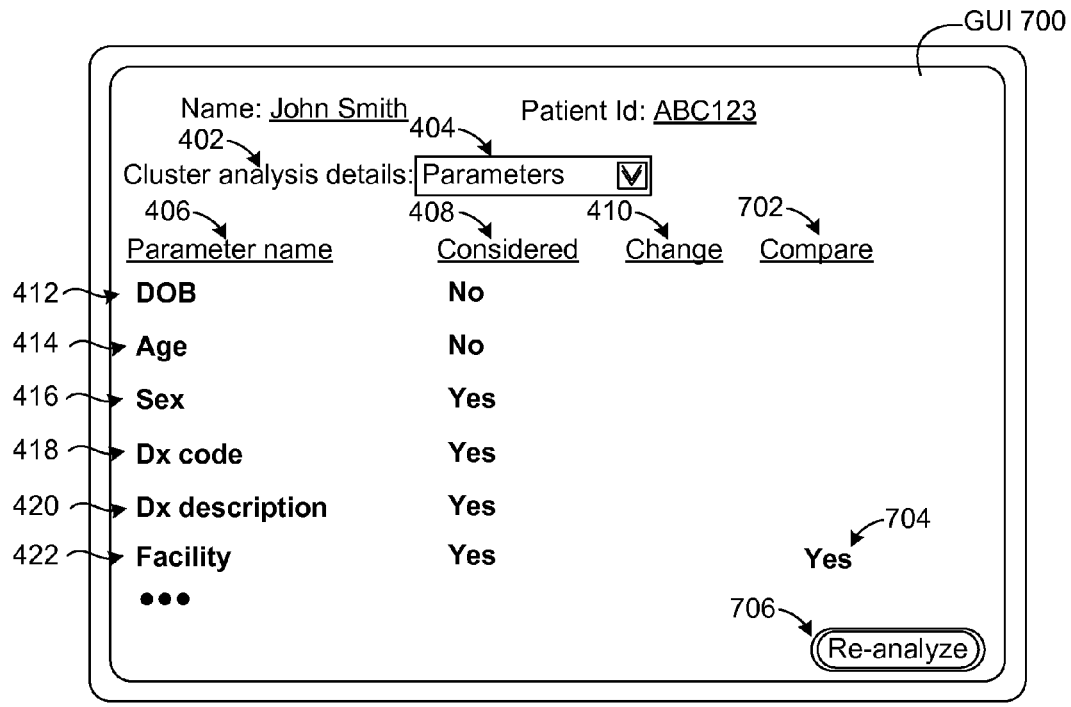

FIG. 7 shows a GUI 700 that can be generated responsive to the clinician wanting more details and clicking box 310 of FIG. 3. GUI 700 includes many of the same features discussed above relative to FIG. 4. For sake of brevity these features are not re-introduced here. GUI 700 also includes a compared column 702. The compare column can allow the clinician (and/or another user, such as an administrator or researcher) to specify an individual parameter upon which a cluster analysis comparison can be performed. For instance, in this case, assume that the clinician wants to know if there are disposition differences between facilities (e.g., would a given patient receive the same treatment at different facilities). This feature can be useful to allow individual facilities to maintain their own protocols rather than being forced to adhere to a universally applied protocol. Another applicability of this feature is that it can be used to determine if protocols employed by one facility produce better patient outcomes than protocols employed by another facility. In this example, as indicated at 704, the clinician can enter 'yes' at the intersection of the facility row 422 and the compare column 702. The clinician can then click the re-analyze button as indicated at 706.

The present implementations can also leverage the patient disposition information to improve patient care. For instance, the clinician can request a notification, such as a text or email message, whenever one of his/her patients moves from one cluster to another.

Figure 8:
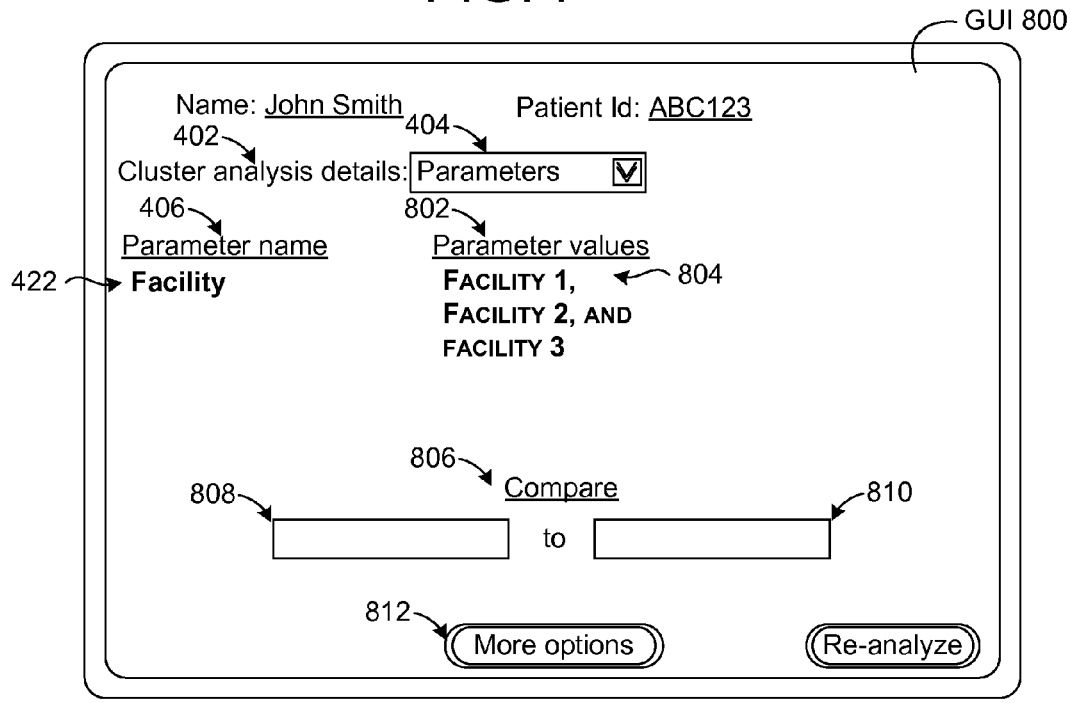

FIG. 8 shows a GUI 800 generated responsively to the user action described above relative to FIG. 7. In the parameter name column 406, the GUI shows the selected parameter name as "facility" (which is the selected parameter from FIG. 7) in row 422. GUI 800 also includes a parameter values column 802 which lists the parameter values for the selected facility parameter. In this case, as indicated at 804 the parameter values are "facility 1", "facility 2", and "facility 3". At 806, the GUI provides a compare feature for the parameter values listed at 802. The user can enter two of the parameter values at 808 and 810 to have a comparison performed. If the user desires another configuration, such as the option of comparing three parameter values, the user can select the more options button at 812. Assume in this example, that the clinician wants to compare facility 1 to facility 3. Accordingly, the clinician enters these parameter values at 808 and 810.

As used herein, "facility" can mean any location, team or organization that can provide treatment. A hospital may be thought of as a facility that can be compared to other facilities. In another sense a hospital may be thought of as including multiple facilities, such as the ER, the ICU ward, non-ICU ward, among others. Of course an exhaustive list of potential parameters is not provided here. In one example, cluster analysis can be used to compare treatment efficacy within a facility (e.g., night shift versus day shift or non-ICU ward versus ICU ward). Viewed another way, facilities may be related to other parameters, such as institutions, or geographic regions, among others. For example, a first institution could include multiple hospitals while a second institution could include other hospitals. Cluster analysis could be performed for the first and second institutions to allow comparisons of the effectiveness of their treatments or protocols. In another case, clustering could be performed on institutions in Washington State and on institutions in Oregon to allow comparison of protocols employed by the two states. The skilled artisan should recognize other variations that can be accomplished with the present cluster analysis concepts.

Figure 9:
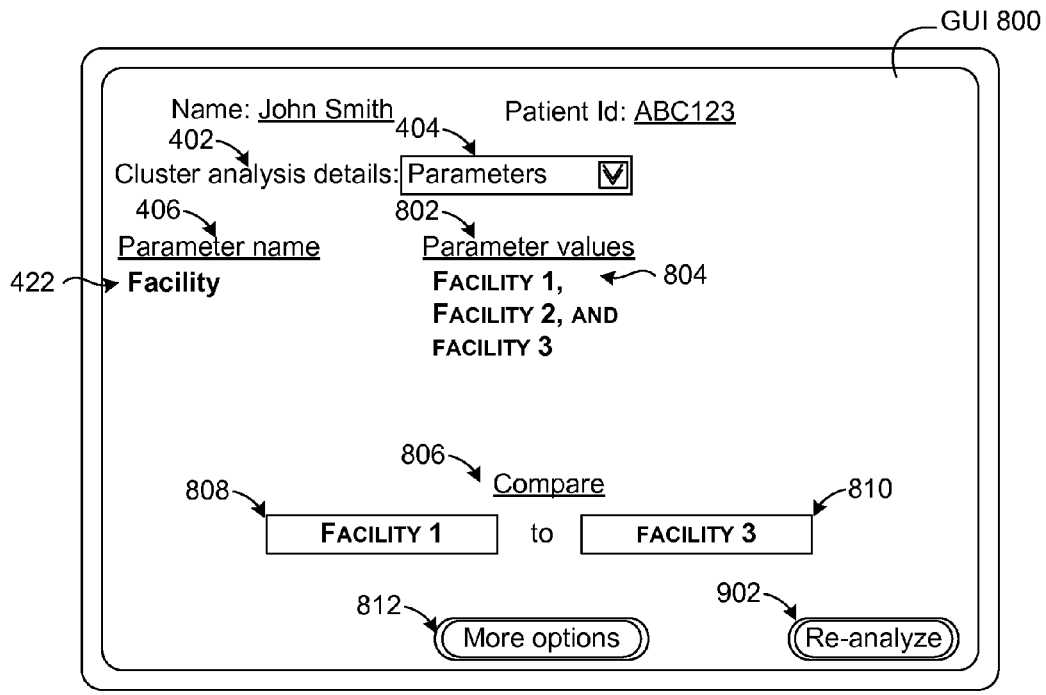

FIG. 9 shows a subsequent view of GUI 800 where the clinician has entered facility 1 at 808 and facility 3 at 810. The clinician can then click the re-analyze button at 902. In this case, re-analyzing can cause the available patient files to be sorted into two sub-groups: those associated with facility 1 and those associated with facility 3. Cluster analysis can then be performed on each sub-group and the results compared.

Figure 10:
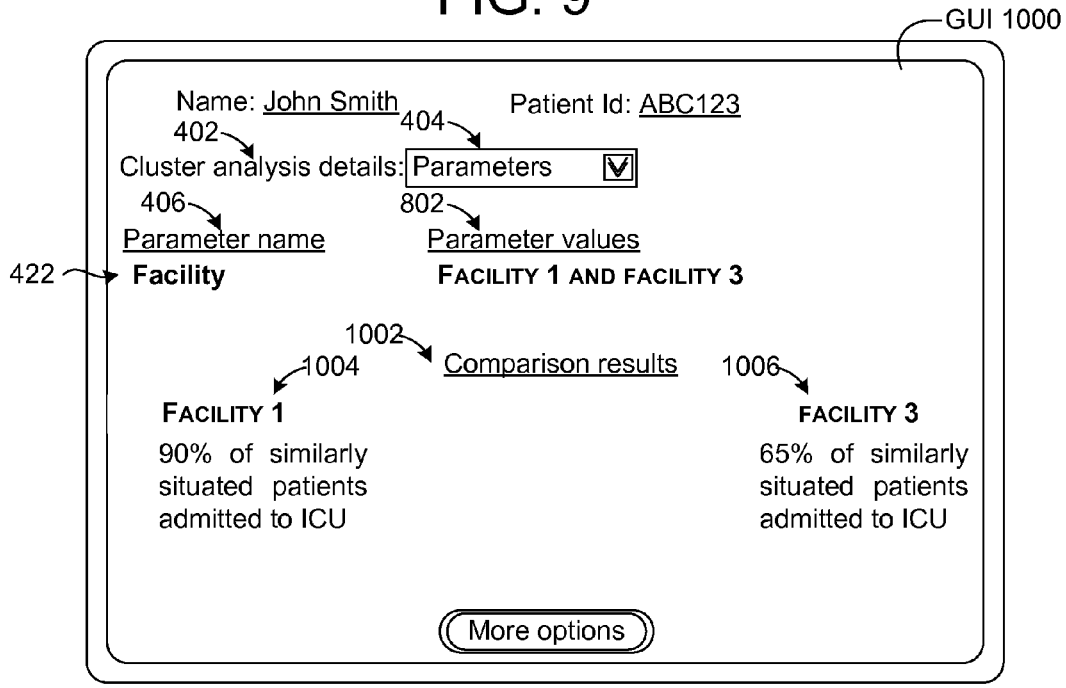

FIG. 10 shows another GUI 1000. This GUI includes the comparison results at 1002. Specifically, the results show at 1004 that cluster analysis performed on the facility 1 sub-group indicates that "90% of similarly situated patients are admitted to the ICU". In contrast, the results show at 1006 that cluster analysis performed on the facility 3 sub-group indicates that "65% of similarly situated patients are admitted to the ICU". This comparison can provide useful information regarding the efficacy of protocols or training at the two facilities.

Figure 11:
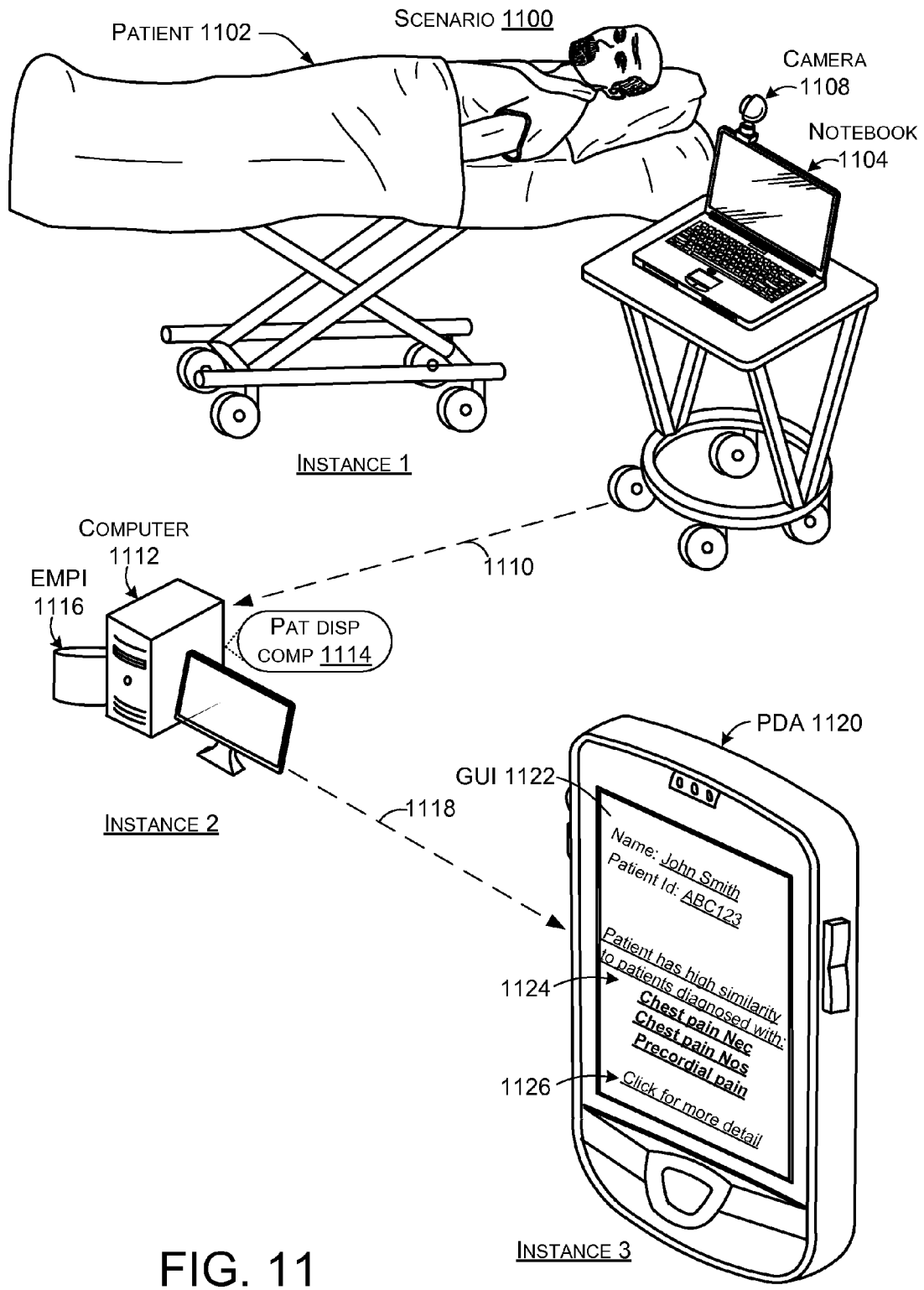
Figure 12:
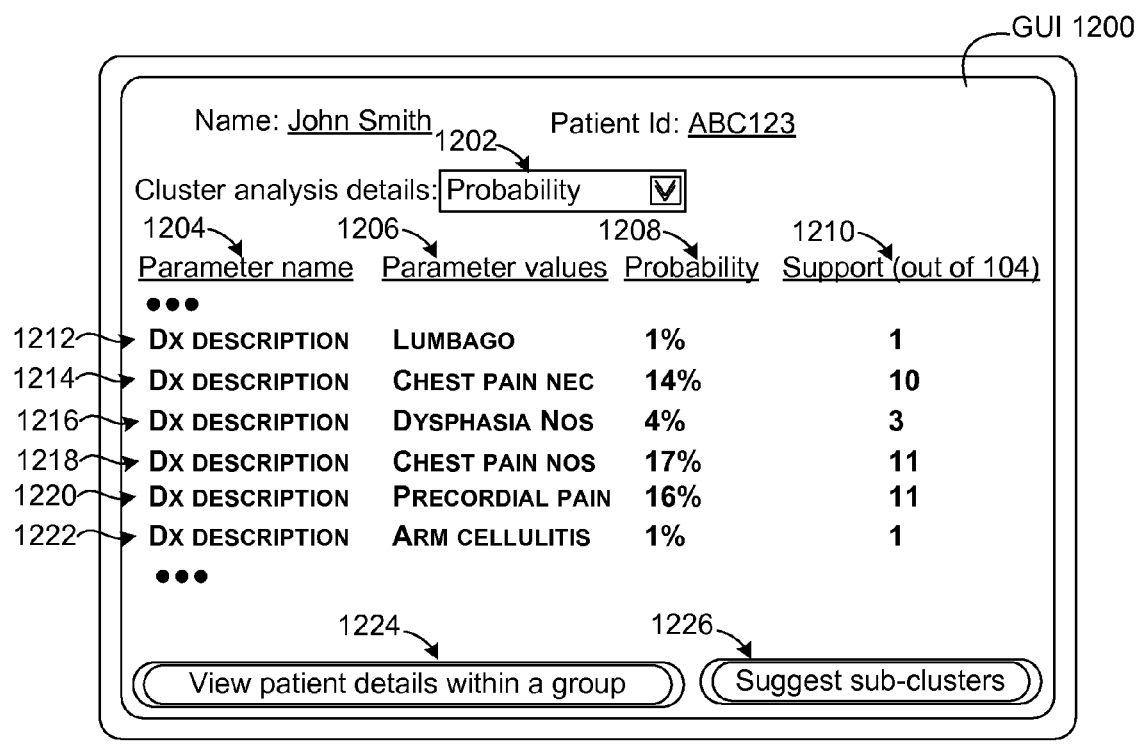

FIGS. 11-12 collectively illustrate another scenario 1100 in which automated patient disposition processing can be employed. FIG. 11 is described relative to instances 1-3 in a similar fashion to FIGS. 1 and 2 above. FIG. 12 is another GUI produced responsive to instance 3 of FIG. 11.

In scenario 1100, a patient 1102 presents for care. The patient is named John Smith, is male, 46 years old and has an unknown condition (DxDescription) and is complaining of chest pain. These parameters can be manually entered into notebook computer 1104, such as by an emergency medical technician, nurse, or other care giver that can triage the patient. Alternatively or additionally, some parameters may be automatically obtained and entered into the notebook, such as by camera 1108 which can capture images of the patient. Other examples of auto-capture parameters can include Electrocardiography (EKG) data and eye color, among others. As indicated by arrow 1110, the captured parameters can be sent to computer 1112.

In instance 2, computer 1112 can include a patient disposition component 1114. This computer can also access an EMPI 1116. Computer 1112 and EMPI 1116 can be manifested as traditional identifiable hardware components or may be manifest as cloud-based resources.

Patient disposition component 1114 can search the EMPI 1116 and employ cluster analysis to identify patients like patient 1102. In this case, the patient disposition component has previously employed cluster analysis on patient files in the EMPI to group patients by similarities. For purposes of example, assume that out of all clusters, one showed the highest relative similarity to patient 1102. The cluster's most frequent (or relevant) characteristics can be presented on a GUI that is intended for a clinician responsible for care of patient 1102. As indicated by arrow 1118, patient disposition component 1114 can cause the GUI to be presented to the clinician.

Instance 3 shows the clinician's personal digital assistant (e.g., smart phone) 1120 receiving and displaying GUI 1122 received from computer 1112 via arrow 1118. In this case at 1124, GUI 1122 indicates that John Smith has a high similarity to patients diagnosed with chest pain not elsewhere classified (Nec), chest pain not otherwise specified (Nos), and Precordial Pain. This information can be utilized by the clinician in developing a diagnosis for John Smith and/or for prioritizing John Smith relative to other patients, among other uses. The clinician can view more details by clicking at 1126.

Note that in this implementation, GUI 1122 can be presented to the clinician before the clinician even sees patient 1102. In this case, the information generated by the patient disposition component 1114 can be thought of as a resource for the clinician. This configuration can be useful in an everyday setting and can be even more valuable in an emergency setting, such as in a mass-casualty setting. This configuration can alternatively or additionally be used as an early warning error detection system or "rescue triage" system that automatically detects potential errors in patient care.

FIG. 12 shows another GUI 1200 generated responsive to the clinician clicking for more details at 1126 of FIG. 11. GUI 1200 shows a partial listing of parameters utilized to generate the information presented on GUI 1122. As indicated at 1202, GUI 1200 shows cluster analysis details relating to probability (e.g., probability of matching the parameters of John Smith). The GUI includes a parameter name column 1204, a parameter value column 1206, a probability column 1208, and a support column 1210 which shows the number of patients in the cluster as 104. For purposes of explanation, rows 1212-1222 relate to the Dx description parameter. Of course other parameters from the patient files can be visualized. In row 1212, the parameter value is "lumbago", the probability is "1%" and the support is "1". Thus, according to the cluster analysis results, in a cluster of 104 patients that potentially matches John Smith, one patient was diagnosed with lumbago and the likelihood of John Smith having lumbago is one-percent. The highest probability of a match occurs in rows 1214, 1218, and 1220. The results presented on GUI 1122 were derived from these three relatively high ranking rows. The clinician may be satisfied with this level of detail as an aid to diagnosing John Smith. Alternatively, the clinician may want to more closely examine the parameters (e.g., files) of patients from individual groups of patients represented by rows 1212-1222. For instance, if the clinician is interested in the patients of row 1214 (e.g., patients that had chest pain nec), the clinician can highlight that row. The clinician can then click the "view patient details within a group" button at 1224. This feature can then provide more details from the patients of the group for the clinician to study. Alternatively, if the clinician thinks there are too many patients in the cluster (in this case 104) the clinician can click the "suggest sub-clusters" option at 1226 to find ways to reduce the number of patients that are members of the presented cluster.

System Example

Figure 13:
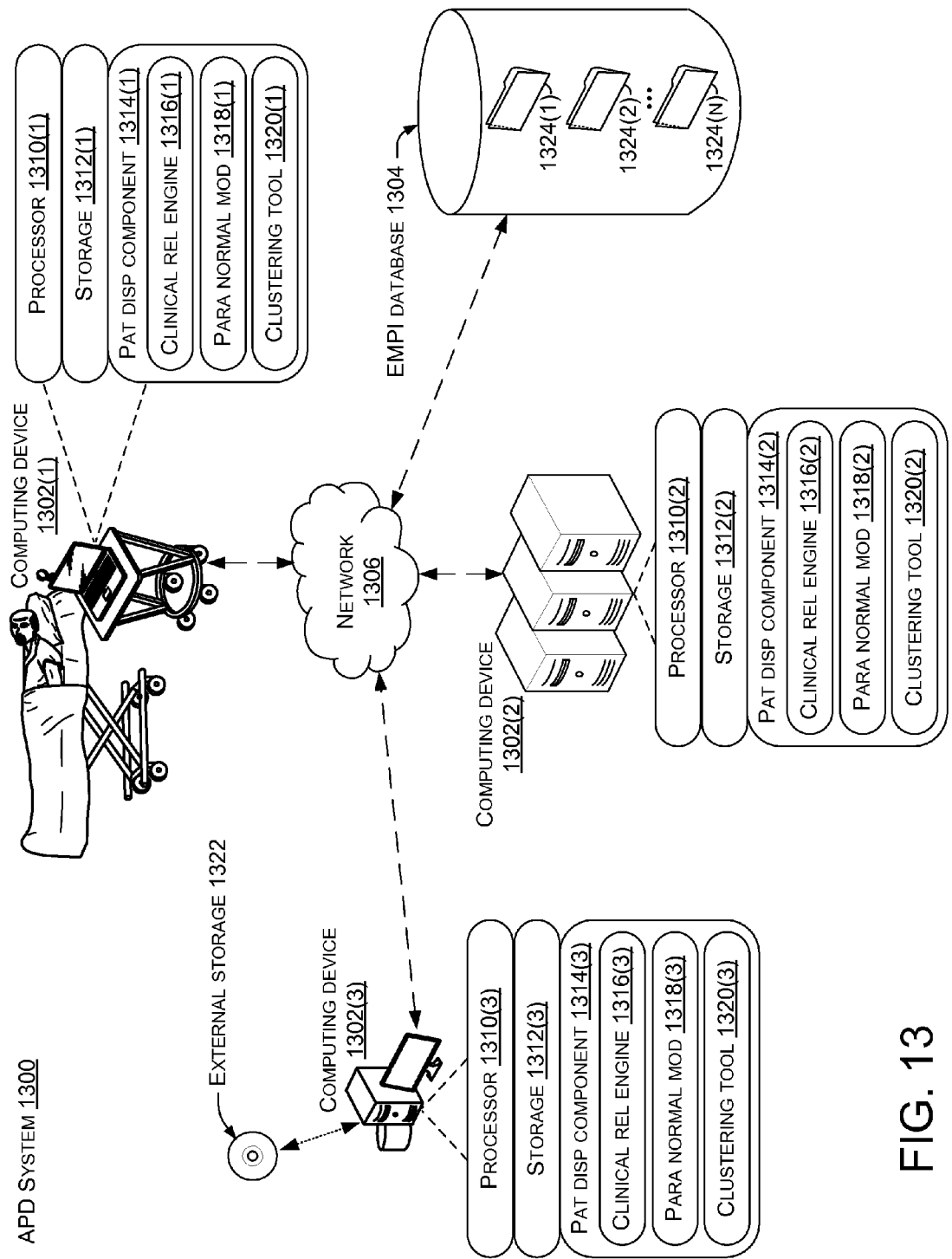
FIG. 13 shows an example of an automated patient disposition system in accordance with some implementations of the present concepts.

FIG. 13 shows an example of an automated patient disposition system (APD system) 1300. Example APD system 1300 can include one or more computing device(s) 1302. For purposes of explanation, APD system 1300 includes three computing devices 1302(1), 1302(2), and 1302(3). APD system 1300 also includes or accesses an electronic master patient index (EMPI) database 1304. The various computing devices 1302(1)-1302(3) and the EMPI database 1304 can communicate over one or more networks 1306, such as, but not limited to, the Internet. (In the discussion of FIG. 13, a suffix '(1)', '(2)', etc., is utilized to indicate an occurrence of a specific element, such as a computing device 1302(1). Generic references to these elements do not include a suffix).

The term "computer" or "computing device" as used herein can mean any type of device that has some amount of processing capability. Examples of computing devices can include traditional computing devices, such as personal computers, cell phones, smart phones, personal digital assistants, or any of a myriad of ever-evolving or yet to be developed types of computing devices. Further, the APD system 1300 can be manifest on a single computing device or distributed over multiple computing devices.

In this case, any of computing devices 1302 can include a processor 1310, storage 1312, and a patient disposition component 1314. In this example, the patient disposition component can include a clinical relevancy engine 1316, a normalization module 1318, and a clustering tool 1320.

Processor 1310 can execute data in the form of computer-readable instructions to provide a functionality. Data, such as computer-readable instructions, can be stored on storage 1312. The storage can include any one or more of volatile or non-volatile memory, hard drives, and/or optical storage devices (e.g., CDs, DVDs etc.), among others. The computing devices 1302 can also be configured to receive and/or generate data in the form of computer-readable instructions from an external storage 1322.

Examples of external storage 1322 can include optical storage devices (e.g., CDs, DVDs etc.), hard drives, and flash storage devices (e.g., memory sticks or memory cards), among others. In some cases, patient disposition component 1314 can be installed on individual computing devices 1302 during assembly or at least prior to delivery to the consumer. In other scenarios, patient disposition component 1314 can be installed by the consumer, such as a download available over network 1306 and/or from external storage 1322. In various implementations, patient disposition component 1314 can be implemented as software, hardware, and/or firmware, or other manner.

The EMPI database 1304 can include and/or reference patient files 1324(1)-1324(N). Each patient file can be associated with a unique identifier or patient identifier. Each patient file can include patient information. At least some of the patient information can manifest as patient parameters that can be obtained and utilized by the patient disposition component 1314.

For purposes of explanation, assume that patient information is received at computing device 1302(1). Computing device 1302(1) may transmit the patient information to the patient's file, for example 1324(1) in the EMPI database 1304.

Clinical relevancy engine 1316 can be configured to identify parameters that are available from patient files in the EMPI. The clinical relevancy engine can select a sub-set of the available patient parameters that are potentially relevant to treatment of the patient. The clinical relevancy engine can obtain values for the selected sub-set of patient parameters from the EMPI. An example of such a process is discussed above relative to FIG. 4. In some implementations the clinical relevancy engine can also allow a user to adjust the individual patient parameters included in the sub-set. An example of such a process is discussed above relative to FIGS. 4-5.

Parameter normalization module 1318 can be configured to normalize values of patient parameters of the sub-set. For instance, parameter values may have been recorded with different instruments and/or utilizing different scales. The parameter normalization module can adjust such parameters to allow more meaningful comparison.

Clustering tool 1320 can be configured to identify similarities between patients based upon the normalized values. The clustering tool can employ one or more clustering algorithms to the patient parameters obtained from the clinical relevancy engine. Some implementations can leverage clustering algorithms employed by data mining engines. For instance, such implementations can leverage data mining engines available on Microsoft SQL Server® brand database management software or database management software available from Oracle® Corp., among others.

In some implementations, the clustering tool 1320 can identify similarities between the patient and other patients. The clustering tool can compare the similarity to a predetermined similarity threshold. The clustering tool may cause disposition information for those patients that satisfy the predetermined similarity threshold to be presented on a GUI. An example of such a process is described above relative to FIG. 11. This GUI can be utilized by a caregiver, such as clinician as an aid to making patient care decisions. The GUI can be utilized by an administrator in an attempt to maintain quality control and/or as a teaching resource.

Note that in some cases cluster analysis may determine similarity to other patients based upon a relatively few patient parameters. In such a case, a human user may readily discern how the similarity was derived. However, in other instances cluster analysis may be based upon tens or hundreds of patient parameters, and each patient parameter may be weighted differently. As a result a human user can readily follow the qualitative result that the patient is more likely a match with one sub-set of patients or another. However, the human user may not be able to quantitatively follow the calculations performed by the clustering algorithms to achieve the qualitative determination.

For ease of explanation, a fully functional patient disposition component 1314 is shown on each computing device 1302 in FIG. 13. This configuration can allow each computer to accomplish the described functionality by accessing the EMPI database 1304 without reliance on other computing devices. In other scenarios, some or all of the functionality may be performed on one computing device, but presented on another computing device. For instance, computing device 1302(1) could be manifest as a thin client that is used for data entry and display purposes. The data could be communicated to computing device 1302(2) which could perform a back-end server role. Computing device 1302(2) can communicate with EMPI database 1304 and process the patient parameters utilizing clinical relevancy engine 1316(2), normalization module 1318(2), and clustering tool 1320(2). Computing device 1302(2) can generate a GUI that reflects the cluster analysis and cause the GUI to be presented on thin client computing device 1302(1). Other system configurations can be employed in various implementations.

Method Examples

Figure 14:
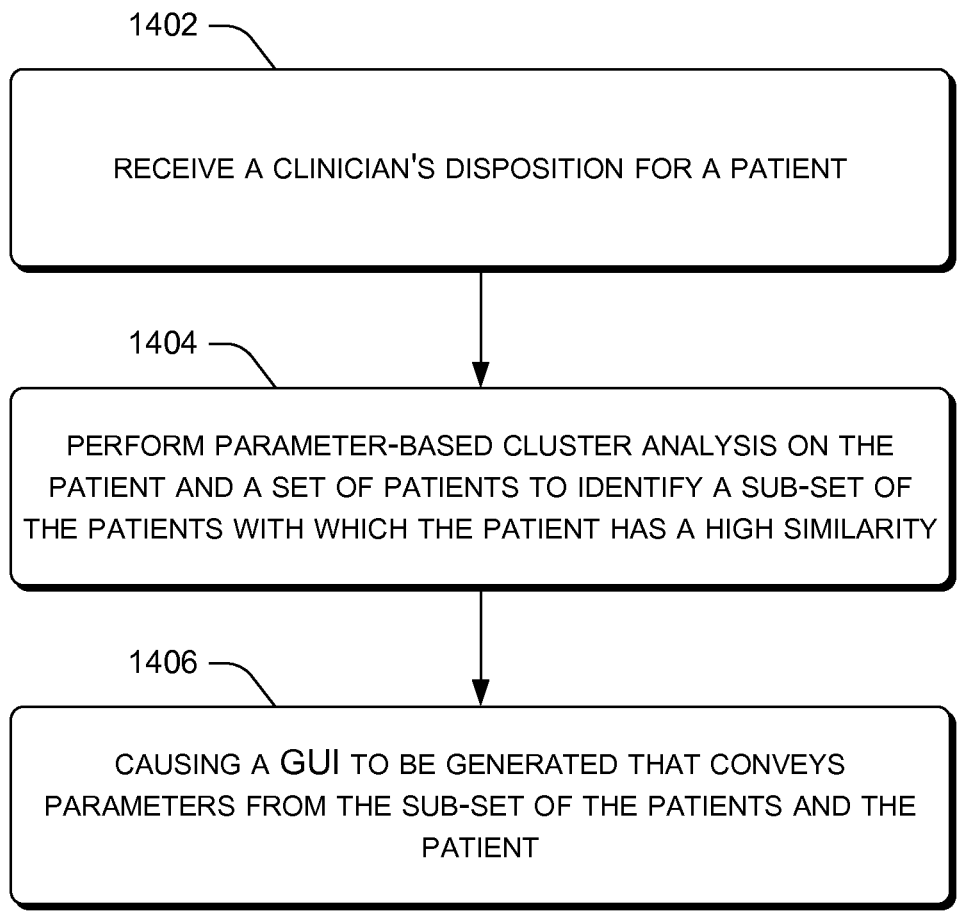
FIG. 14 shows an example flowchart of automated patient disposition methods in accordance with some implementations of the present concepts.

FIG. 14 illustrates a flowchart of an automated patient disposition technique or method 1400. Other methods are described above by way of example relative to FIGS. 1-12.

At block 1402, the method can receive a clinician's disposition for a patient.

At block 1404, the method can perform parameter-based cluster analysis on the patient and a set of patients to identify a sub-set of the patients with which the patient has a high similarity. In one case, the set of patients can be obtain from a listing of patients. One relatively formal patient listing can be maintained in an EMPI index, but other less formal patient indexes may be utilized.

At block 1406, the method can cause a GUI to be generated that conveys parameters from the sub-set of the patients and the patient.

The order in which the example methods are described is not intended to be construed as a limitation, and any number of the described blocks or steps can be combined in any order to implement the methods, or alternate methods. Furthermore, the methods can be implemented in any suitable hardware, software, firmware, or combination thereof, such that a computing device can implement the method. In one case, the method is stored on one or more computer-readable storage media as a set of instructions such that execution by a computing device causes the computing device to perform the method.

CONCLUSION

Although techniques, methods, devices, systems, etc., pertaining to automated patient disposition are described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:
1. A method, comprising:
receiving patient values of one or more parameters, wherein the patient values of the one or more parameters are associated with a patient;
performing parameter-based cluster analysis on the patient and a set of patients, the performing comprising:
identifying a first sub-set of the set of patients having an associated first disposition and a second sub-set of the set of patients having an associated second disposition, wherein the first sub-set has first values for the one or more parameters and the second sub-set has second values, different from the first values, for the one or more parameters, and,
determining that the patient fits in the first sub-set rather than the second sub-set based on similarity of the patient values for at least some of the one or more parameters to the first values for the one or more parameters; and, causing a graphical user interface (GUI) to be generated that conveys:
    that the patient fits in the first sub-set that is associated with the first disposition,
    the one or more parameters utilized in the cluster analysis and other patient parameters that were excluded from the cluster analysis, and
    the patient values for the one or more parameters,
wherein the causing further includes generating an option to change some of the one or more parameters utilized in the cluster analysis,
and further wherein at least the performing and the causing are performed by a computing device.

2. The method of claim 1, wherein the performing occurs before the receiving of a clinician's disposition for the patient, or wherein one of the parameters used in the performing is the clinician's disposition, or wherein the performing is repeated after receiving the clinician's disposition.

3. The method of claim 1, wherein the causing further includes causing the first disposition associated with the first sub-set to be presented.

4. The method of claim 1, wherein the GUI further includes an option to further differentiate the first sub-set of the set of patients into multiple sub-clusters.

5. A system, comprising:
a display device;
a clinical relevancy engine configured to:
    select a sub-set of available patient parameters that are potentially relevant to treatment of a patient,
    cause individual patient parameters included in the sub-set to be presented on a graphical user interface (GUI) on the display device, and
    allow a user to interact with the GUI to adjust values of the individual patient parameters included in the sub-set;
a parameter normalization module configured to normalize the values of the patient parameters of the sub-set;
a clustering tool configured to:
    identify similarities between the patient and other patients based upon the normalized values,
    compare the similarities to a predetermined similarity threshold, and
    cause disposition information for individual patients of the other patients that satisfy the predetermined similarity threshold to be presented on a subsequent GUI as an aid for the user in making patient care decisions; and,
at least one processor configured to execute the clustering tool.

6. The system of claim 5, wherein the clinical relevancy engine is configured to obtain the available patient parameters from an electronic master patient index.

7. The system of claim 5, wherein the individual patient parameters include at least one parameter relating to a treatment facility and wherein the user can compare care between different treatment facilities or within an individual treatment facility via the clustering tool.

\* \* \* \* \*